(12) United States Patent
Banerjee

(10) Patent No.: US 6,921,817 B1
(45) Date of Patent: Jul. 26, 2005

(54) METHODS FOR SIMULTANEOUS ISOLATION OF BIOLOGICALLY ACTIVE TRANSCRIPTION FACTORS AND DNA

(76) Inventor: Ranjit Banerjee, 655 Mildred St., Teaneck, NJ (US) 07666

( * ) Notice: Subject to any disclaimer, the term of this patent is extended or adjusted under 35 U.S.C. 154(b) by 0 days.

(21) Appl. No.: 09/635,027

(22) Filed: Aug. 4, 2000

Related U.S. Application Data
(60) Provisional application No. 60/147,270, filed on Aug. 5, 1999.

(51) Int. Cl.[7] .......................... C07H 21/00; C12Q 1/68; C07K 1/00; A23J 1/00
(52) U.S. Cl. .......................... 536/25.4; 435/6; 530/350; 530/412
(58) Field of Search .............................. 435/6; 536/25.4, 536/23.1; 935/76, 77, 78; 530/350, 412

(56) References Cited

PUBLICATIONS

Das et al., Methods in Molecular Biology. vol. 1, No. 5/6, pp. 213–222 (1990).*
Dingnam et al. Nucleic Acids Researchy 11(5) : 1475–1489 (1983).*
Kadonaga et al., PNAS 83 : 5889–5893 (1986).*
Pizzella et al., DNA and Cell Biology 13(1) : 67–74 (1994).*
Caruccio et al., J. of Immunilogical Methods 230 : 1–10 (1999).*
Caruccio L., Ph.D. Dissertation, The Graduate School of Biomedical Sciences, Robert Wood Johnson Medical School (May 1995).*
Karpen et al., Mol. Cell. Biol. 8 : 5159 (1988).*
Caruccio L., Dissertaion Abstract, Diss Abstr. Int. B 1995, 56(7), 3735.*
Caruccio et al., J. of Immunological Methods 230 : 1–10 (Nov. 1999).*
Dignam et al., Nucleic Acids Research 11(5) : 1475–1489 (1983).*

* cited by examiner

*Primary Examiner*—Ethan Whisenant
(74) *Attorney, Agent, or Firm*—Arthur I. Degenholtz

(57) ABSTRACT

A rapid isolation method permits the isolation of DNAs, RNAs and transcription factors simultaneously from a wide range of lymphoid and non-lymphoid cells, either from patients or in culture, without the loss of biological activity. A significant advantage of this method is that it entails minimal handling of samples from the patients with various disease states and pathogenic conditions such as AIDS, hepatitis, and other infectious diseases, which require substantial precautions during isolation of DNAs and proteins.

4 Claims, 14 Drawing Sheets

1    Collecting and maintaining cells at a concentration in the range of 1-2 X $10^5$/ml in culture medium,

2    Treating cells with at least one test compound,

3    Collecting the cell by scapping and by centrifuging at 1,000 rpm for 5 min in a table top centrifuge,

4    Washing the cell pellets twice with 5 ml ice cold PBS, (phosphate buffered saline, pH 7.4) by centrifuging the cells again at 1,000 rpm,

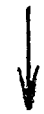

5    Resuspending the cell pellets, transferring to a first Eppendorf tube in 1 ml of ice cold PBS,

*Fig. 4 A*

6    Centrifuging at 2,000 rpm for 5 min at 4 °C removing the PBS processing the cell pellets following according to the protein and DNA isolation steps comprising,

7    Preparing Buffer A: (cell lysis buffer), [20 mM Hepes, pH 7.9, 10 mM NaCl, 3 mM $MgCl_2$, 0.1% NP-40, 10% glycerol, 0.2 mM EDTA, 1 mM dithiothreitol (DTT), 0.4 mM phenylmethylsulfonyl fluoride (PMSF), antipain (1 µg/ml), leupeptin (1 µg/ml)],

8    Preparing Buffer B: (extraction buffer without salt), [20 mM Hepes, pH 7.9, 0.2 mM EDTA, 20% glycerol, 1 mM DTT, 0.4 mM PMSF, antipain (1 µg/ml), leupeptin (1 µg/ml)],

9    Preparing Buffer C: (extraction buffer with salt), [20 mM Hepes, pH 7.9, 400 mM NaCl, 0.2 mM EDTA, 20% glycerol, 1 mM DTT, 0.4 mM PMSF, antipain (1 µg/ml), leupeptin (1 µg/ml)],

*Fig. 4 B*

10 Preparing Buffer D: (cytoplasmic extraction clarification buffer), [20 mM Hepes, pH 7.9, 400 mM NaCl, 0.2 mM EDTA, 40% glycerol, 1 mM DTT, 0.4 mM PMSF, antipain (1 µg/ml), leupeptin (1 µg/ml)],

11 Performing Simultaneous isolation of protein and DNA comprising the steps of,

12 Resuspending the cell pellets in 100-125 µl (2 pellet vol) of Buffer A,

13 Maintaining the resuspended cell pellets on ice for 10-15 min with occasional tapping,

14 Pelleting the nuclei by centrifuging at 2,000 rpm for 5 min at 4°C,

15 Removing the cytoplasmic supernatant fraction to a second Eppendorf tube,

*Fig. 4 C*

16 Quick freezing on dry ice in a -86 °C freezer and store for future use,

17 Washing the bottom nuclear fraction with 200-300 μl Buffer B to remove NP-40, 18 Centrifuging at 2,000 rpm for 5 min at 4 °C, 19 Resuspending the pelleted nuclei into 100-130 μl high salt Buffer C on ice for 45 min and mixing periodically by tapping to extract the nuclear proteins, 20 Centrifuging the nuclear fraction in an Eppendorf centrifuge at 13,000 rpm for 15 min at 4 °C, 21 Removing the supernatents, aliquoted, in 25 μl and quick freezing on dry ice, 22 Storing at -86 °C,

*Fig. 4 D*

23 Quick freezing the remaining pellet containing nucleic acids and other debris,

24 Storing at -86 °C,

25 Clarifying the cytoplasmic fraction by adding 1/3 vol of

Buffer D to this fraction for 30 min at 4 °C to equilibrate the cytoplasmic proteins with NaCl,

26 Centrifuging at 13,000 rpm for 15 min.,

27 Removing and quick freezing the supernatants and storeing at -

86 °C,

28 Performing DNA extraction and analysis comprising the steps of,

29 Thawing frozen cell pellets from on ice for 10 min,

30 Adding 100μl of Buffer [0.1 % SDS, 10 mM Tris-HCl, pH 7.9, 10 mM EDTA, 10 mM NaCl] for 15 min,

*Fig. 4 E*

31 Mixing using wide bore Eppendorf pipet tips,

32 Adding RNAase A for 2 h at 37 °C with gentle tapping every 30 min,

33 Adding proteinase K [200 μl /ml] for 2 h at 37 °C with gentle tapping every 30 min, 34 Extracting with an equal volume of TE (10 mM Tris-HCl, 1 mM EDTA, pH 8.0) saturated phenol, 35 Removing the upper aqueous layer was removed to another tube, 36 Performing back extractions twice with 50 μl of TE, 37 Collecting the DNA solutions in a fresh tube, 38 Adding an equal volume of phenol/chloroform (50:50) mixture, 39 Mixing by inverting repeatedly,

*Fig. 4 F*

49 Staining the DNA gel with ethidium bromide,

50 Photographing with UV light,

51 Radiolabeling of the sequence specific oligonucleotides comprising the steps of,

52 Synthesizing single stranded oligonucleotides on a DNA synthesizer and annealing with the complimentary strand by combining 4 µg of both strands in a tube with total volume of 30 µl of annealing buffer (5 mM NaCl, 10 mM Tris-HCl and 0. 2 mM EDTA),

53 boiling the tubes for 5 min and slowly cooling to room temperature for 6 h,

54 Heating the tubes to 55 °C for 5 min and then cooling on ice for 10 min,

55 Quantitating 4 µl aliquot of the annealed oligos at 260 λ and storing the remainder at -20 °C until radiolabeled,

*Fig. 4 H*

56 Preparing probes by radiolabeling 200 ng of annealed oligonucleotide in 15 µl of total volume containing 50 µCi of [γ-$^{32}$P]ATP (6,000 Ci/mmol), 20 Units of T4 polynucleotide kinase, and 1.5 µl 10X T4 polynucleotide kinase buffer for 1 h at 37 °C,

↓

57 Filling in the 5' over-hang ends with 5 Units of Klenow with 3.0 µl of 10X Klenow buffer and 0.15 mM each of dATP, dCTP, dGTP, and dTTP for 40 min at 37 °C in a reaction volume of 30 µl.

↓

58 Increasing the volume to 1 ml with sterile TE with 200 mM NaCl, pH 8.0, and the labeled oligonucleotides were purified on a NACS Prepac column, to separate the unincorporated nucleotides,

↓

59 Precipating the labeled, purified oligonucleotides overnight with 3 vol absolute ethanol at -20 °C,

60 Centrifuging at 13,000 rpm for 1 h and then vacuum drying,

61 Resuspending the labeled oligonucleotide probes in 100 µl of sterile 0.1X TE buffer and storing at -20 °C,

62 Electrophoretic mobility shift assay,

63 Incubating 5 µg of nuclear or cytoplasmic extract, for each reaction, with 0.2-0.3 ng of [γ-$^{32}$P]ATP labeled oligonucleotide probe containing either NF-κB sequence (5'-gatccGGGACTTTCCGCTGGGGACTTTCCG-3') (SEQ ID NO 1) or an AP-1 consensus sequence including the PMA responsive element indicated in bold (5'-gatccGTGACTCAGCGCG-3') (SEQ ID NO 2),

64 Adding 3 µg of poly(dI-dC):poly(dI-dC) as a non-specific competitor and incubating with the nuclear extracts for 10 min prior to the addition of the radiolabeled probe,

*Fig. 4J*

65 Adding antibodies against p65, p50, c-*Fos* or c-*Jun* to the respective binding reactions for supershift assays and incubating at room temperature for 1.5 h, prior to probing with $[\gamma\text{-}^{32}P]$ATP labeled oligonucleotide for an additional 25 min at room temperature, 66 Separating the bound complexes on either a 5%, for supershift assays, or 6%, for analytical purposes, acrylamide/bis (30:1 ratio) native gel as required and runing at 200v for 3.5 h with 0.25X TBE (0.02 M Tris-borate, 0.5 mM EDTA) as running buffer at room temperature, 67 Vacuum drying the gel with heat at 80 °C and exposing them to Kodak X-OMAT film for 3-12 hours, 68 Analyzing the bound and free DNA protein complexes.

*Fig. 4 K*

SEQUENCE LISTING

<160> NUMBER OF SEQ ID NOS: 2

<210> SEQ ID NO 1
<211> LENGTH: 30
<212> TYPE: DNA
<213> ORGANISM: Human immunodeficiency virus

<400> SEQUENCE: 1
gatccgggac tttccgctgg ggactttccg                                        30

<210> SEQ ID NO 2
<211> LENGTH: 18
<212> TYPE: DNA
<213> ORGANISM: Human immunodeficiency virus

<400> SEQUENCE: 2
gatccgtgac tcagcgcg                                                     18

METHODS FOR SIMULTANEOUS ISOLATION OF BIOLOGICALLY ACTIVE TRANSCRIPTION FACTORS AND DNA

CROSS REFERENCE TO RELATED APPLICATIONS

This application is based on a Provisional Patent Application of Ranjit Banerjee, Ser. No. 60/147,270 filed on Aug. 5, 1999, titled "Methods for simultaneous isolation of biologically active transcription factors and DNA".

STATEMENT OF FEDERALLY SPONSORED RESEARCH

Work leading to the present invention was supported by National Institutes of Health (NIH) grants CA56302 and DA429259 awarded to Ranjit Banerjee.

FIELD OF THE INVENTION

The present invention relates primarily to the field of DNA isolation and nuclear and cytoplasmic cell extracts and more particularly to a rapid and efficient method for simultaneous isolation of biologically active transcription factors and DNA.

BACKGROUND OF THE INVENTION

In order to effectively characterize the gene modulation and transcriptional regulation in eukaryotic cells as well as in various diseases it is necessary to isolate the DNAs and the specific proteins, known as transcription factors (Mitchell and Tjian, 1989; Crabtree and Clipstone, 1994; and Rao et al., 1997), either from tissue samples obtained from different disorders or the cells collected from them grown in culture. The DNAs and proteins isolated from various sources must be intact and undegraded in order to be analyzed by various molecular techniques to evaluate their roles in pathogenic processes. It is often necessary to isolate various DNAs and proteins from a large number of samples over a short time period to determine when a specific gene activation occurs via modulation of a transcription factor, and to utilize them as land marks for identification of different disorders. However, such procedures are generally difficult and cumbersome. Most importantly these proteins should bind to specific DNA sequence motifs (Singh et al., 1985; Sen and Baltimore, 1986a,b; Gilman, et al., 1986; Angel, et al., 1987; Pierce, et al., 1988; Rauscher et al., 1988; Smeal, et al., 1989) and also be recognizable by specific antibodies. Over the past years, various protocols have been developed for the isolation of DNAs as well as the nuclear and cytoplasmic proteins which are involved in transcriptional modulation (Dignam et al., 1983a,b; Kadonaga and Tjian, 1986; Karpen, et al., 1988; Sambrook, et al., 1989; Fiering et al., 1990). However, the majority of these protocols require several steps of purification and high speed centrifugation which involves a significant time lapse between the collection of samples, and substantial physical contact with the laboratory workers. Moreover, the simultaneous isolation of DNAs and transcription factors is rather difficult in a short time span, which is an important aspect, for a sequential evaluation of gene modulation.

The following references define the present state of the art.

Angel, P. and Karin, M. 1991. The role of Jun, Fos and the AP-1 complex in cell-proliferation and transformation. Biochim. Biophys. Acta. 1072, 129.

Angel, P., Imagawa, M., Chiu, R., Stein, B., Imbra, R. J., Rahmsdorf, H. J., Joant, C., Herrlich, P., and Karin, M. 1987. Phorbol ester-inducible genes contain a common cis element recognized by a TPA-modulated trans-acting factor. Cell 49, 729.

Baldwin, A. S., Jr. 1996. The NF-κB and IκB proteins: new discoveries and insights. Annu. Rev. Immunol. 14, 649.

Banerjee, R., Bekesi, G. J., Tarcsafalvi, A., Sperber, K., Deak, G., Choi, H. S. H., Paronetto, F., Holland, J. F., and Acs, G. 1992. Productive nonlytic human immunodeficiency irus type 1 replication in a newly established human leukemia cell line. Proc. Natl. ad. Sci. USA 89, 9996.

Banerjee, R., Karpen, S., Siekevitz, M., Lengyel, G., Bauer, J., and Acs, G. 1989. Tumor necrosis factor-alpha induces a kappa B sequence-specific DNA-binding protein in human hepatoblastoma HepG2 cells. Hepatology 10, 1008.

Bekesi, J. G., Banerjee, R., Jiang, J. D., Roboz, J. P., Tarcsafalvi, A., Holland, J. F., and Acs, 1995. Translocation of cytoplasmic antigenic markers in a biphenotypic cell line derived from a patient with myelodysplastic syndrome. Mol. Cell. Diff 3, 111.

Caputo, A., Sodroski, J. G., and Haseltine, W. A. 1990. Constitutive expression of HIV-1 tat protein in human jurkat T cells using a BK virus vector. J. Acquired Immune Defic.Syndr. 3, 372.

Crabtree, G. R. and Clipstone, N. A. 1994. Signal transmission between the plasma membrane and nucleus of T lymphocytes. Annu. Rev. Biochem. 63, 1045.

Crothers, D. M. 1987. Gel electrophoresis of protein-DNA complexes. Nature 325, 464.

Dignam, J. D., Lebovitz, R. M., and Roeder, R. G. 1983a. Accurate transcription initiation by RNA polymerase II in a soluble extract from isolated mammalian nuclei. Nucleic Acids Res. 11, 1475.

Dignam, J. D., Martin, P. L., Shastry, B. S., and Roeder, R. G. 1983b. Eukaryotic gene transcription with purified components. Methods Enzymol. 101, 582.

Fiering, S., Northrop, J. P., Nolan, G. P., Mattila, P. S., Crabtree, G. R., and Herzenberg, L. A. 1990. Single cell assay of a transcription factor reveals a threshold in transcription activated by signals emanating from the T-cell antigen receptor. Genes Dev. 4, 1823.

Fried, M. G. 1989. Measurement of protein-DNA interaction parameters by electrophoresis mobility shift assay. Electrophoresis 10, 366.

Fried, M. and Crothers, D. M. 1981. Equilibria and kinetics of lac repressor-operator interactions by polyacrylamide gel electrophoresis. Nucleic Acids Res. 9, 6505.

Garner, M. M. and Revzin, A. 1981. A gel electrophoresis method for quantifying the binding of proteins to specific DNA regions: application to components of the *Escherichia coil* lactose operon regulatory system. Nucleic Acids Res. 9, 3047.

Garner, M. M. and Revzin, A. 1986. The use of gel electrophoresis to detect and study nucleic acid-protein interactions. Trends in Biochem. Sci. 11, 395.

Gilman, M. Z., Wilson, R. N., and Weinberg, R. A. 1986. Multiple protein-binding sites in the 5'-flanking region regulate c-fos expression. Mol. Cell. Biol. 6, 4305.

Innis, M. A., Gelfand, D. H., Sninsky, J. J., and White, T. J. 1990. PCR protocols: a guide to methods and applications. Academic Press. San Diego, Calif.

Kadonaga, J. T. and Tjian, R. 1986. Affinity purification of sequence-specific DNA binding proteins. Proc. Natl. Acad. Sci. USA 83, 5889.

Karpen, S., Banerjee, R., Zelent, A., Price, P., and Acs, G. 1988. Identification of protein-binding sites in the hepatitis B virus enhancer and core promoter domains. Mol. Cell. Biol. 8, 5159.

Knowles, B. B., Howe, C. C., and Aden, D. P. 1980. Human hepatocellular carcinoma cell lines secrete the major plasma proteins and hepatitis B surface antigen. Science 209, 497.

Lee, W., Mitchell, P., and Tjian, R. 1987. Purified transcription factor AP-1 interacts with TPA-inducible enhancer elements. Cell 49, 741.

Mitchell, P. J. and Tjian, R. 1989. Transcriptional regulation in mammalian cells by sequence-specific DNA binding protein. Science 245, 371.

Miyamoto, S. and Verma, I. M. 1995. Rel/NF-κB/IκB story. Adv. Cancer Res. 66, 255.

Northrop, J. P., Ullman, K. S., and Crabtree, G. R. 1993. Characterization of the nuclear and cytoplamsic components of the lymphoid-specific nuclear factor of activated T cells (NF-AT) complex. J. Biol. Chem. 268, 2917.

Piatak, M., Jr., Luk, K. C., Williams, B., and Lifson, J. D. 1993a. Quantitative competitive polymerase chain reaction for accurate quantitation of HIV DNA and RNA species. Biotechniques 14, 70.

Piatak, M., Jr., Saag, M. S., Yang, L. C., Clark, S. J., Kappes, J. C., Luk, K. C., Hahn, B. H., Shaw, G. M., and Lifson, J. D. 1993b. High levels of HIV-1 in plasma during all stages of infection determined by competitive PCR. Science 259, 1749.

Pierce, J. W., Lenardo, M., and Baltimore, D. 1988. Oligonucleotide that binds nuclear factor NF-κB acts as a lymphoid-specific and inducible enhancer element. Proc. Natl. Acad. Sci. USA 85, 1482.

Pizzella, T. and Banerjee, R. 1994. Identification of a human immunodeficiency virus type 1 TAR binding protein in human hepatoblastoma HepG2 cells that trans-activates HIV-1 LTR-directed gene expression. DNA Cell Bio. 13, 67.

Rao, A., Luo, C., and Hogan, P. G. 1997. Transcription factors of the NFAT family: regulation and function. Annu. Rev. Immunol. 15, 707.

Rauscher, F. J., III, Sambucetti, L. C., Curran, T., Distel, R. J., and Spiegelman, B. M. 1988. Common DNA binding site for Fos protein complexes and transcription factor AP-1. Cell 52, 471.

Saha, K., Sova, P., Chao, W., Chess, L., and Volsky, D. J. 1996. Generation of CD4+ and CD8+ T-cell clones from PBLs of HIV-1 infected subjects using herpesvirus saimiri. Nature Med. 2, 1272.

Sambrook, J., Fritsch, E. F., and Maniatis, T. 1989. Molecular cloning: a laboratory manual, 2nd ed. Cold Spring Harbor Laboratory Press. Cold Spring Harbor, N.Y.

Sen, R. and Baltimore, D. 1986a. Multiple nuclear factors interact with the immunoglobulin enhancer sequences. Cell 46, 705.

Sen, R. and Baltimore, D. 1986b. Inducibility of ê immunoglobulin enhancer-binding protein NF-κB by a post-translational mechanism. Cell 47, 921.

Singh, H., Sen, R., Baltimore, D., and Sharp, P. A. 1986. A nuclear factor that binds to a conserved sequence motif in transcriptional control elements of immunoglobulin genes. Nature 319, 154.

Smeal, T., Angel, P., Meek, J., and Karin, M. 1989. Different requirements for formation of Jun:Jun and Jun:Fos complexes. Genes Dev. 3, 2091.

Starcich, B., Ratner, L., Josephs, S. F., Okamoto, T., Gallo, R. C., and Staal, F. W. 1985. Characterization of long terminal repeat sequences of HTLV-III. Science 227, 538.

Weiss, A., Wiskocil, R. L., and Stobo, J. D. 1984. The role of T3 surface molecules in the activation of human T cells: a two-stimulus requirement for IL-2 production reflects events occuring at a pre-translational level. J. Immunol. 133, 123.

OBJECTS AND SUMMARY OF THE INVENTION

It is an object of the present invention to provide a rapid and efficient method for simultaneous isolation of biologically active transcription factors and DNA.

Another object of the present invention is to provide a method for simultaneous isolation of biologically active transcription factors and DNA which requires minimal handling of samples from the patients with various disease states and pathogenic conditions such as AIDS, hepatitis, and other infectious diseases, which require substantial precautions during isolation of DNAs and proteins.

Another object of the present invention is to provide a method for simultaneous isolation of biologically active transcription factors and DNA which is a fast and efficient way to prepare various cellular proteins.

Another object of the present invention is to provide a method for simultaneous isolation of biologically active transcription factors and DNA which permits multiple sample collection over a short time span for sequential analysis of gene activation.

Another object of the present invention is to provide a method for simultaneous isolation of biologically active transcription factors and DNA in which there is no requirement for expensive or specialized equipment such as ultracentrifuges or sonicators.

Another object of the present invention is to provide a method for simultaneous isolation of biologically active transcription factors and DNA in which physical contact and manipulation steps are minimized, providing additional safety in the preparation of samples from biologicaly hazardous infectious patients or cells treated with toxic chemical components.

Another object of the present invention is to provide an efficient method for sample collection from patients at various stages of their disease and to evaluate them at a desirable time to collect and analyze a comparative data.

Another object of the present invention is to provide a method for simultaneous isolation of biologically active transcription factors and DNA which is capable of isolating proteins and DNAs simultaneously from each sample so that it is possible to analyze the alterations in DNA modification as well as related changes in the transcriptional proteins. Isolation of RNAs can also be achieved by modifing this method.

Another object of the present invention is to provide a method for simultaneous isolation of biologically active transcription factors and DNA which provides major advantages over previously published protocols (Dignam et al., 1983a,b; Kadonaga and Tjian, 1986; Fiering et al., 1990; Pizzella and Banerjee, 1994) is that these extracts do not require either extensive manipulation after initial collection, or dialysis of the DNAs and proteins to remove salt or other contaminating reagents.

Yet another object of the present invention is to provide a method for simultaneous isolation of high purity biologically active transcription factors and DNA in which samples prepared by this method can be frozen quickly at −86° C. and then used later.

The foregoing and other objects and advantages of the present invention will appear more clearly hereinafter.

The following abbreviations will be used in the description of the present invention. AIDS, acquired immunodeficiency syndrome; HIV, human immunodeficiency virus; TNF-α, tumor necrosis factor α; PMA, phorbol 12-myristate 13-acetate; Br-cAMP, 8-bromo-adenosine 3':5'-cyclic monophosphate; PBS, phosphate buffered saline; TAE, tris-acetate EDTA; TBE, tris-borate EDTA; FCS, fetal calf serum; DTT, dithiothreitol; PMSF, phenylmethylsulfonyl fluoride; EMSA, electrophoretic mobility shift assay; NF-κB, nuclear factor κB AP-1, activator protein.

In accordance with the present invention there is provided a rapid method for isolation of both transcription factors, also known as transcriptionally active proteins, and DNA without the use of any expensive high-speed centrifugation. Transcription factors play a crucial role in gene regulation during different stages of eukaryotic development as well as in controlling various cellular disorders involving the immune system. In order to study the role of cellular DNAs and the effects of certain biologically active regulatory proteins, which can affect gene expression, we have developed a rapid and efficient method for preparing highly purified DNAs as well as nuclear and cytoplasmic proteins, simultaneously. These DNAs and proteins can be effectively analyzed to determine their genetic integrity and binding motifs to specific DNA sequences, respectively. This protocol avoids the drastic use of mechanical shearing of cells, aggressive use of detergents or high speed ultracentrifugation steps, as well as facilitating the ease of collecting samples in a sequential and effective manner with minimal time lapse during processing. Such an approach permits the analysis of a large number of samples in a short time. The current technique uses a non-ionic detergent to isolate nuclei, and obtain the cytosolic extract, a low-ionic strength buffer to wash off the detergent and a high-salt buffer to extract nuclear proteins including transcription factors. The remainder of the cellular products are processed for DNA extraction. This method will be particulary useful to evaluate the time course effects of various cell signal transducing biological modifiers such as cytokines or mitogens, as well as drugs and other therapeutic agents or adjuvants used in the treatments of various groups of patients, especially in infectious diseases and also in immunological or neoplastic disorders, with minimal physical contact to the laboratory personnel. This rapid DNA and protein isolation method can be widely used in various systems to analyze the modulation of DNA characteristics and transcriptionally active proteins as biomarkers in different human diseases.

DESCRIPTION OF THE DRAWINGS

Other important objects and advantages of the invention will be apparent from the following detailed description of the invention, taken in connection with the accompanying drawings in which.

DETAILED DESCRIPTION OF THE INVENTION

Figure 1:
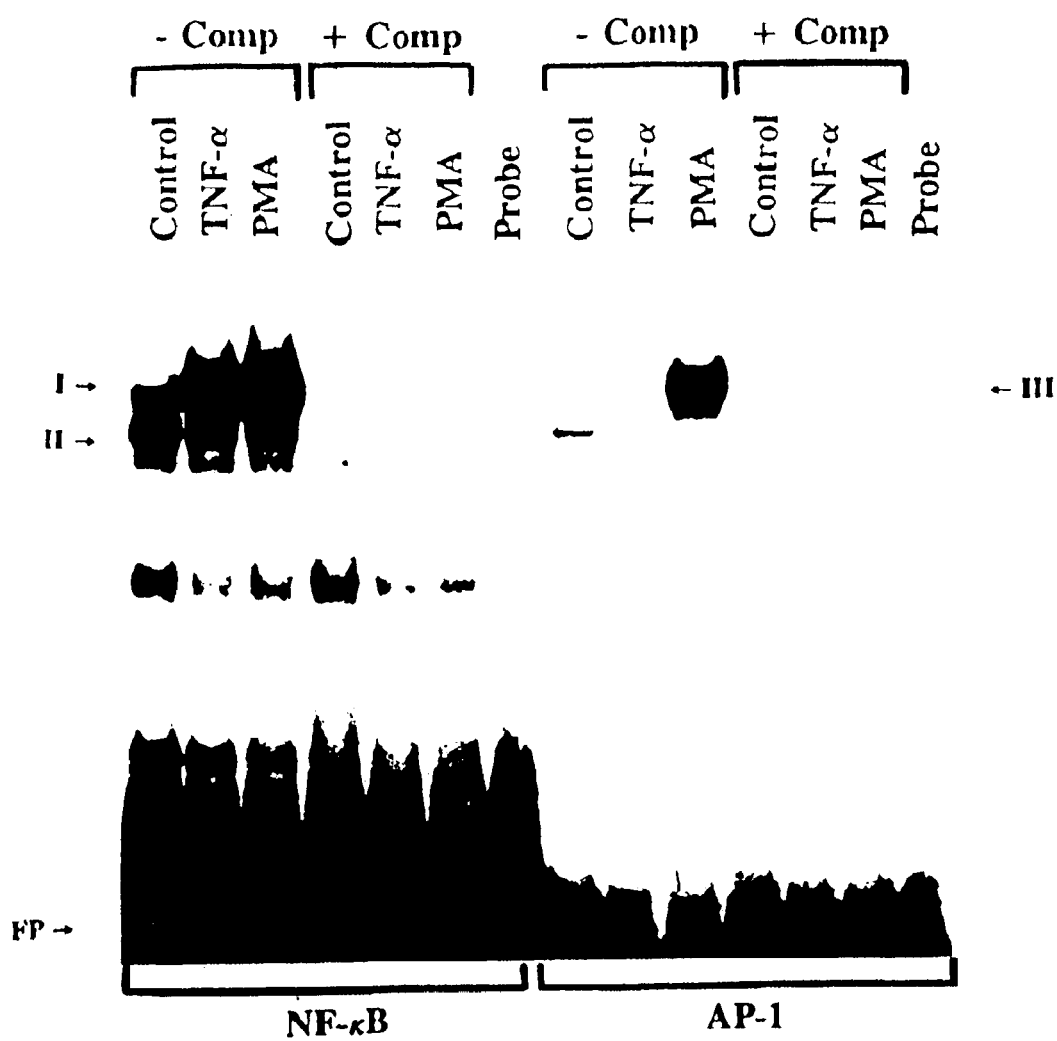
FIG. 1. shows activation of NF-κB (Lanes 2,3) and AP-1 (Lanes 9,10) in MDS cells following 4 h treatment with either TNF-α or PMA, as compared with the untreated controls (Lanes 1 and 8) which show the presence of low levels of constitutive NF-κB and AP-1 in this cell line.

With reference to the drawings, the present invention provides a rapid method modified from the previously published procedure (Karpen et al., 1988; Pizzella and Banerjee, 1994) that requires minimal time and effort and can be accomplished without the use of expensive high speed centrifugation. Furthermore, this method permits the isolation of both DNAs and transcription factors simultaneously from a wide range of lymphoid and non-lymphoid cells, either from the tissues or different organs of the patients, or the cells grown in culture from these tissues, without the loss of biological activity.

1. Advantages of the Method According to the Invention

A significant advantage of this method is that it entails minimal handling of samples from the patients with various disease states and pathogenic conditions such as AIDS, hepatitis, and other infectious diseases, which require substantial precautions during isolation of DNAs and proteins. The DNAs and transcription factors isolated by this method can be successfully used in various molecular assays such as Southern blot analyses, polymerase chain reaction (PCR) or restriction fragment length polymorphisms (RFLP) together with the DNA-protein interactions by electrophoretic mobility shift assays (EMSA), (Fried and Crothers, 1981; Garner and Revzin, 1981; Garner and Revzin, 1986; Crothers, 1987; Fried, 1989; Sambrook, et al., 1989; Innis, et al., 1990; Piatak, et al., 1993a,b; Pizzella and Banerjee, 1994). Using this rapid method we have specifically analyzed the DNA profile and the expression of two transcription factors, NF-κB and AP-1, which are critical in the regulation of a number of genes and their activity is usually modified in different pathological conditions and disease states (Sen and Baltimore, 1986a,b; Lee, et al., 1987; Mitchell and Tjian, 1989; Angel and Karin, 1991; Miyamoto and Verma, 1995; Baldwin, 1996). The isolation and characterization of the protein subunits of these transcription factors supports the efficacy and validity of this methodology.

2. Materials and Methods 2.1 Cell Lines

This isolation protocol has been examined using a number of lymphoid and non-lymphoid cell lines, including Jurkat-E6 (Weiss, et al., 1984), Jurkat-tat (Caputo, et al., 1990), HepG2 (Knowles, et al., 1980; Banerjee, et al., 1989) and various Herpesvirus transformed T cell-derived clones (HVS/TCC) from AIDS patients (Saha, et al., 1996). To develop this method, we have used a well characterized myeloid cell line, MDS, (Banerjee et al., 1992; Bekesi et al., 1995) which was derived from a patient with myelodysplastic syndrome and can be differentiated to lymphoid lineage by treatment with PMA (phorbol 12-myristate 13-acetate) together with Br-cAMP (8-bromo-adenosine 3':5'-cyclic monophosphate). MDS cells were maintained at a concentration of $2 \times 10^5$/ml in Minimal Essential Medium (MEM) with 10% fetal calf serum (FCS), and antibiotics (penicillin-100 units/ml and streptomycin-100 μg/ml) in 5% $CO_2$ at 37° C., Cell culture reagents were purchased from GIBCO/BRL, Grand Island, N.Y.

2.2 Cell Treatment and Collection

MDS cells were treated either with TNF-α, (tumor necrosis factor-α, 200 units/ml, Genzyme, Cambridge, Mass.), PMA, (20 ng/ml, Sigma Chemical Co., St. Louis, Mo.) or PMA (20 ng/ml) combined with Br-cAMP, (200 µg/ml, Sigma Chemical Co., St. Louis, Mo.) for 48 h to ensure differentiation to a lymphoid lineage (Banerjee et al., 1992). Various other cell signaling agents, therapeutic drugs, test compounds and carcinogens has also been used for testing the effectiveness of this method. For each sample, nuclear and cytoplasmic extracts were prepared from $1\times10^7$ cells, which were collected by centrifuging at 1,000 rpm for 5 min in a table top centrifuge and then washing the cell pellets twice with 5 ml ice cold PBS, (phosphate buffered saline, pH 7.4) and centrifuging the cells again at 1,000 rpm. The cell pellets were resuspended and transferred to an Eppendorf tube in 1 ml of ice cold PBS and then centrifuged at 2,000 rpm for 5 min at 4° C. The PBS was removed completely and the cell pellets processed according to the protein and DNA isolation steps described in Sections 2.4 and 2.5. It should be emphasized that monolayer culture cells or macrophages which adhere to cell plates should be collected by using a rubber policeman and gentle tapping but not by trypsinization which degrades the protein moieties.

2.3 Reagent Preparation

Buffer Solutions:

(a): Buffer A: (cell lysis buffer), [20 mM Hepes, pH 7.9, 10 mM NaCl, 3 mM $MgCl_2$, 0.1% NP-40, 10% glycerol, 0.2 mM EDTA, 1 mM dithiothreitol (DTT), 0.4 mM phenylmethylsulfonyl fluoride (PMSF), antipain (1 µg/ml), leupeptin (1 µg/ml)].

(b): Buffer B: (extraction buffer without salt), [20 mM Hepes, pH 7.9, 0.2 mM EDTA, 20% glycerol, 1 mM DTT, 0.4 mM PMSF, antipain (1 µg/ml), leupeptin (1 µg/ml)].

(c): Buffer C: (extraction buffer with salt), [20 mM Hepes, pH 7.9, 400 mM NaCl, 0.2 mM EDTA, 20% glycerol, 1 mM DTT, 0.4 mM PMSF, antipain (1 µg/ml), leupeptin (1 µg/ml)].

(d): Buffer D: (cytoplasmic extraction clarification buffer), [20 mM Hepes, pH 7.9, 400 mM NaCl, 0.2 mM EDTA, 40% glycerol, 1 mM DTT, 0.4 mM PMSF, antipain (1 µg/ml), leupeptin (1 µg/ml)].

2.4 Simultaneous Isolation of Protein and DNA

The cell pellets were resuspended in about 100–125 µl (2 pellet vol) of Buffer A and left on ice for 10–15 min with occasional tapping. The nuclei were pelleted by centrifuging at 2,000 rpm for 5 min at 4° C. The cytoplasmic supernatant fraction was removed to another Eppendorf tube and "snap (quick) frozen" on dry ice and then put into a −86° C. freezer for storage. The nuclei were washed with 200–350 µl Buffer B to remove NP-40 and centrifuged at 2,000 rpm for 5 min at 4° C. The pelleted nuclei were then resuspended into 100–130 µl Buffer C on ice for 45 min with periodic mixing by tapping to extract the nuclear proteins. The nuclear fraction was then centrifuged in an Eppendorf centrifuge at 13,000 rpm for 15 min at 4° C. The supernatents were removed, aliquoted, and quick frozen on dry ice and stored at −86° C. The remaining pellet containing nucleic acids and other debris was also snap frozen and stored at −86° C. or prepared immediately for DNA extraction as described below. If it is necessary to analyze the cytoplasmic fraction for detailed evaluation, it is further clarified by adding ⅓ vol of Buffer D to this fraction for 30 min at 4° C. to equilibrate the cytoplasmic proteins with NaCl, followed by centrifuging at 13,000 rpm for 15 min. The supernatants were snap frozen and stored at −86° C.

2.5 DNA Extraction and Analysis

Frozen cell pellets from undifferentiated and differentiated MDS cells were thawed on ice for 10 min and then 100 µl of Buffer A [0.1% SDS, 10 mM Tris-HCl, pH 7.9, 10 mM EDTA, 10 mM NaCl] was added for 15 min and mixed using wide bore Eppendorf pipet tips. RNAase A [Boehringer Mannheim, Indianapolis, Ind., 100 µg/ml] was added for 2 h at 37° C. with gentle tapping every 30 min. Then proteinase K was added [Boehringer Mannheim, 200 µg/ml] for 2 h at 37° C. with gentle tapping every 30 min followed by extraction with an equal volume of TE (10 mM Tris-HCl, 1 mM EDTA, pH 8.0) saturated phenol. The upper aqueous layer was removed to another tube and back extractions were performed twice with 50 µl of TE and the DNA solutions were collected in a fresh tube. An equal volume of phenol/chloroform (50:50) mixture was added, mixed by inverting repeatedly, then centrifuged at 3,000 rpm for 10 min. The upper aqueous phase was removed, and then extracted with an equal volume of chlorofrom/isoamyl (96:4) alcohol and the resulting upper aqueous phase containing the DNA was precipitated using 0.5 M NaCl and 3 vol of ice cold ethanol at −20° C. The samples were centrifuged at 13,000 rpm for 30 min, the DNA pellets were air dried, and dissolved in 300 µl of 0.1×TE at 37° C. for 4–6 h. If required, the DNA pellets can be dissolved in a warm room on a slow speed shaker overnight to facilitate solubilization.

Ten µg of the high molecular weight DNA from each sample were digested for 4 h with 30 units each of the three restriction enzymes, EcoR I, BamH I, and Hind III (New England Biolabs, Beverly, Mass.), and then electrophoresed on a 0.8% TAE (0.40 M Tris-acetate, 1 mM EDTA) agarose gel. The DNA gel was stained with ethidium bromide and photographed with UV light.

2.6 Radiolabeling of the Sequence Specific Oligonucleotides

Single stranded oligonucleotides synthesized on a DNA synthesizer were annealed with the complimentary strand by combining 4 µg of both strands in a total volume of 30 µl of annealing buffer (5 mM NaCl, 10 mM Tris-HCl and 0.2 mM EDTA) and boiling the tubes for 5 min in 500 ml of water and slowly cooling to room temperature for 6 h. The tubes were then heated to 55° C. for 5 min and then chilled on ice for 10 min. A 4 µl aliquot of the annealed oligos were quantitated at 260 λ and the remainder was stored at −20° C. until radiolabeled. The probes were prepared by radiolabeling 200 ng of annealed oligonucleotide in 15 µl of total volume containing 50 µCi of [$\gamma$-$^{32}$P]ATP (6,000 Ci/mmol, New England Nuclear-DuPont, Boston, Mass.), 20 Units of T4 polynucleotide kinase (New England Biolabs, Beverly, Mass.), and 1.5 µl 10× T4 polynucleotide kinase buffer (NEB, Beverly, Mass.) for 1 h at 37° C., followed by filling in the 5' over-hang ends with 5 Units of Klenow (NEB, Beverly, Mass.) with 3.0 µl of 10× Klenow buffer (NEB, Beverly, Mass.), and 0.15 mM each of dATP, dCTP, dGTP, and dTTP (Boehringer Mannheim, Indianapolis, Ind.), for 40 min at 37° C. in a reaction volume of 30 µl. The volume was increased to 1 ml with sterile TE with 200 mM NaCl, pH 8.0, and the labeled oligonucleotides were purified on a NACS Prepac column (Life Technologies, Rockville, Md.) following the manufacturer's instructions to separate the unincorporated nucleotides. The labeled, purified oligonucleotides were precipitated overnight with 3 vol absolute ethanol at −20° C., centrifuged at 13,000 rpm for 1 h and then vacuum dried. The labeled oligonucleotide probes were resuspended in 100 µl of sterile 0.1×TE buffer and stored at −20° C.

2.7 Electrophoretic Mobility Shift Assay

Electrophoretic mobility shift assays (EMSA) with nuclear protein extracts and radiolabeled NF-κB and AP-1 probes were performed using a previously published protocol (Karpen et al., 1988; Banerjee et al., 1989; Pizzella and Banerjee, 1994) with certain modifications. Briefly, 5 μg of nuclear extract was used for each reaction with 0.2–0.3 ng of [γ-$^{32}$P]ATP labeled oligonucleotide probe containing either NF-κB sequence (Starcich et al., 1985) from HIV-1 LTR (5'-gatccGGGACTTTCCGCTGGGGACTTTCCG-3') (SEQ ID NO 1) or an AP-1 consensus sequence (Northrop et al., 1993) including the PMA responsive element indicated in bold (5'-gatccGTGACTCAGCGCG-3') (SEQ ID NO 2). For each DNA-protein binding reaction 3 μg of poly(dI-dC):poly(dI-dC) was used as a non-specific competitor and incubated with the nuclear extracts for 10 min prior to the addition of the radiolabeled probe. For supershift assays, antibodies against p65, p50, c-Fos or c-Jun (Santa Cruz Biotechnology, Santa Cruz, Calif.) were added to the respective binding reactions and incubated at room temperature for 1.5 h, prior to probing with [γ-$^{32}$P]ATP labeled oligonucleotide for an additional 25 min at room temperature. The bound complexes were separated on either a 5% or 6% acrylamide/bis (30:1 ratio) native gel as required and run at 200v for 3.5 h with 0.25×TBE (0.02 M Tris-borate, 0.5 mM EDTA) as running buffer at room temperature and then vacuum dried with heat at 80° C. and exposed to Kodak X-OMAT film (Eastman Kodak, Rochester, N.Y.). Specifically, the 5% gels were used for assays that included antibodies for, optimal separation of the bound protein complexes, whereas, 6% gels were critical for resolving various specific and non-specific bands more precisely.

3. Results 3.1 Activation of NF-κB and Detection of its p65 and p50 Subunits

Figure 2:
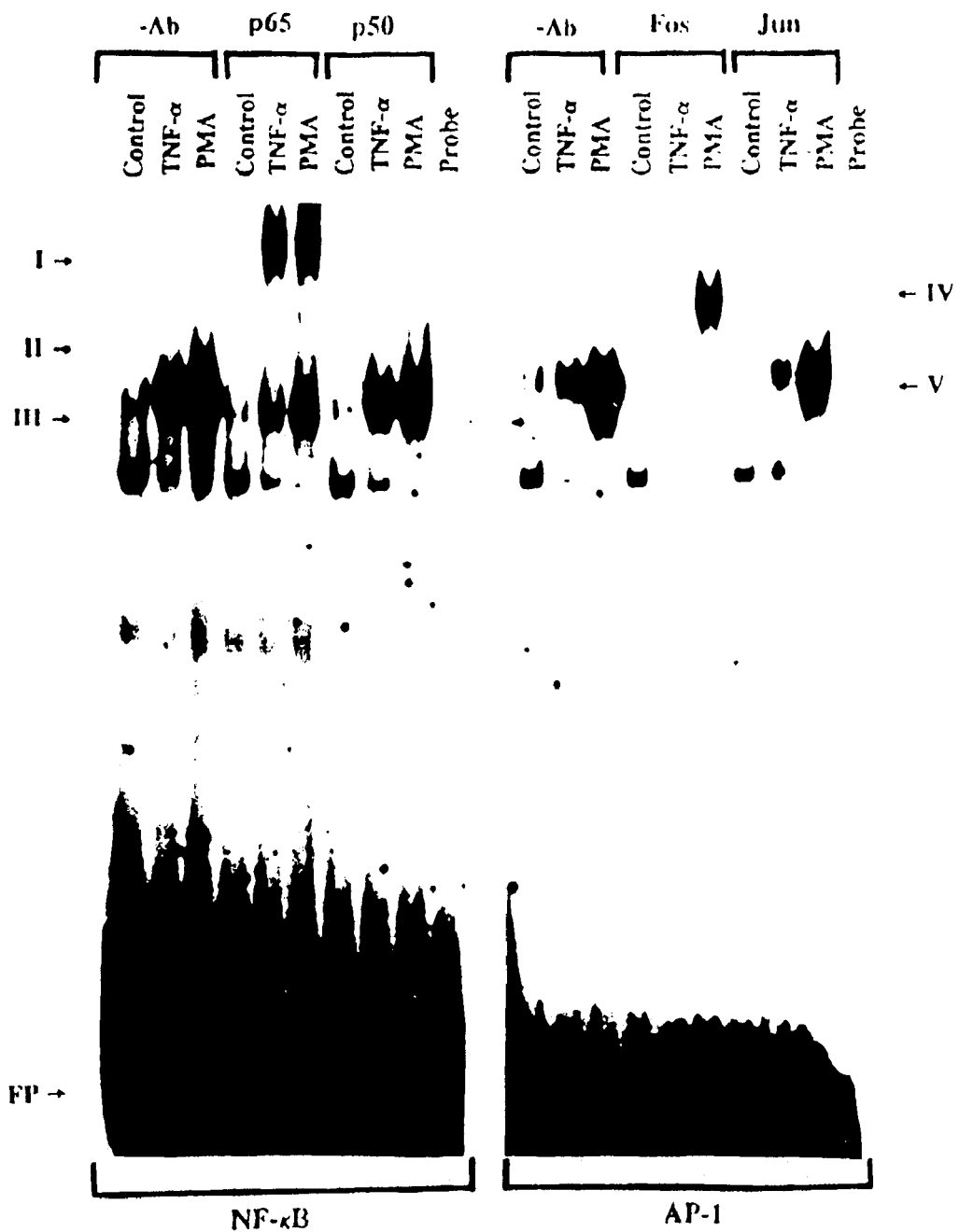
FIG. 2. is a super shift assay showing the expression of the NF-κB (Lanes 1–10) or AP-1 (Lanes 11–20) protein subunits in MDS cells treated for 4 h with either TNF-α or PMA detected using specific antibodies as compared to the extracts without any antibody (Lanes 1–3 and 11–13).

Using this rapid protein isolation method we successfully demonstrated the binding of MDS nuclear extracts to the radiolabed NF-κB probe in an EMSA (FIGS. 1, 2). Cells were treated with TNF-γ or PMA for 4 h to stimulate activation of NF-κB complex as compared to untreated MDS cells used as a control. The activation of NF-κB with either TNF-α or PMA treatment was about 8 and 10 fold, respectively, as compared to the untreated control (FIG. 1, Lanes 1–3). The high level of activation by both TNF-α and PMA in a short treatment period correlated well with the data obtained using other protocols (data not shown). Competition EMSAs with a 50-fold molar excess of unlabeled oligonucleotide as competitor demonstrated the specificity of binding for NF-κB probes (FIG. 1, Lanes 4–6).

In order to demonstrate that the different components of transcription factors isolated by this method are intact in this extract and can be recognized by their specific antibodies, we have performed supershift assays to illustrate the presence of p65 (Rel A) and p50 (NF-κB1) in the NF-κB binding complexes. The bound complex observed in FIG. 1 contained both p65 and p50 fractions for both TNF-α and PMA treated extracts. The shifted fractions contained a much higher amount of p65 complex (I) as compared to p50 for both TNF-α and PMA treated cell extracts (FIG. 2, Lanes 5,6 and 8,9, respectively). Although no p50 complex (II) was visible, a reduction of bound complex (III) due to the reaction with p50 specific antibody substantiates the presence of this complex in these extracts (FIG. 2, Lanes 8,9). The distinct presence of p65 band (I) with TNF-α or PMA, and a reduction of bound band (III) with p50 antibody on the gel (FIG. 2), indicated that there was no significant damage to the proteins present in the complex and, importantly, no formation of aggregation during preparation.

3.2 Activation of AP-1 and Identification of the Fos and Jun Complexes

The binding of nuclear extracts from TNF-α or PMA treated cells to a radiolabeled AP-1 consensus sequence probe was analyzed by an EMSA. In addition to the NF-κB activation the level of AP-1 induced by 4 h of PMA treatment was very high compared to the untreated control or TNF-α treated sample (FIG. 1, Lanes 8–10). Although AP-1 activation due to 4 h of TNF-α treatment was much lower than that observed following PMA treatment, it was slightly higher than the untreated control as resolved in the 5% gel (FIG. 2, Lanes 11–13), thus indicating the validity of using two different gel compositions for specific purposes. The competition EMSAs with a 50-fold molar excess of unlabeled AP-1 oligonucleotide showed the specificity of this binding (FIG. 1, Lanes 11–13). These results clearly demonstrate that transcription factors prepared by this technique can accurately bind to their respective specific sequence motifs.

In order to demonstrate the various components of the AP-1 complex, namely, c-Fos and c-Jun, the nuclear extracts were analyzed by supershift assays by incubating with antibodies against c-Fos and c-Jun. Both TNF-α and PMA treated samples showed the presence of c-Fos and c-Jun epitopes since the bound complexes present in the corresponding antibody treated lanes (FIG. 2, Lanes 14–19) were significantly reduced as compared to the untreated samples (FIG. 2., Lanes 11–13). Specifically, a strongly shifted complex due to c-Fos antibody was revealed only in the PMA treated sample (FIG. 2, Lane 16), whereas TNF-α treated samples had significantly reduced bands for both c-Fos and c-Jun, as compared to the TNF-α treated extract without antibody (FIG. 2, Lanes 12, 15 and 18). It is evident that the binding epitopes for c-Fos and c-Jun remain intact throughout processing of the cell samples and during the assay to detect binding activity.

3.3 Analysis of the DNA Profile

The undigested DNA profile of the undifferentiated MDS cells (FIG. 3, Lane 3) or MDS cells differentiated for 48 h (FIG. 3, Lane 7) showed that there was no degradation of the DNAs during processing in either of these samples and that their molecular weight was higher than 23 kb. These DNAs were completely digested with EcoR I, BamH I, or Hind III, respectively, (Lanes 4–6 and 8–10) indicating that these samples are free from protein and other Contaminants and can optimally recognize the specificity of these restriction enzymes.

Figure 3:
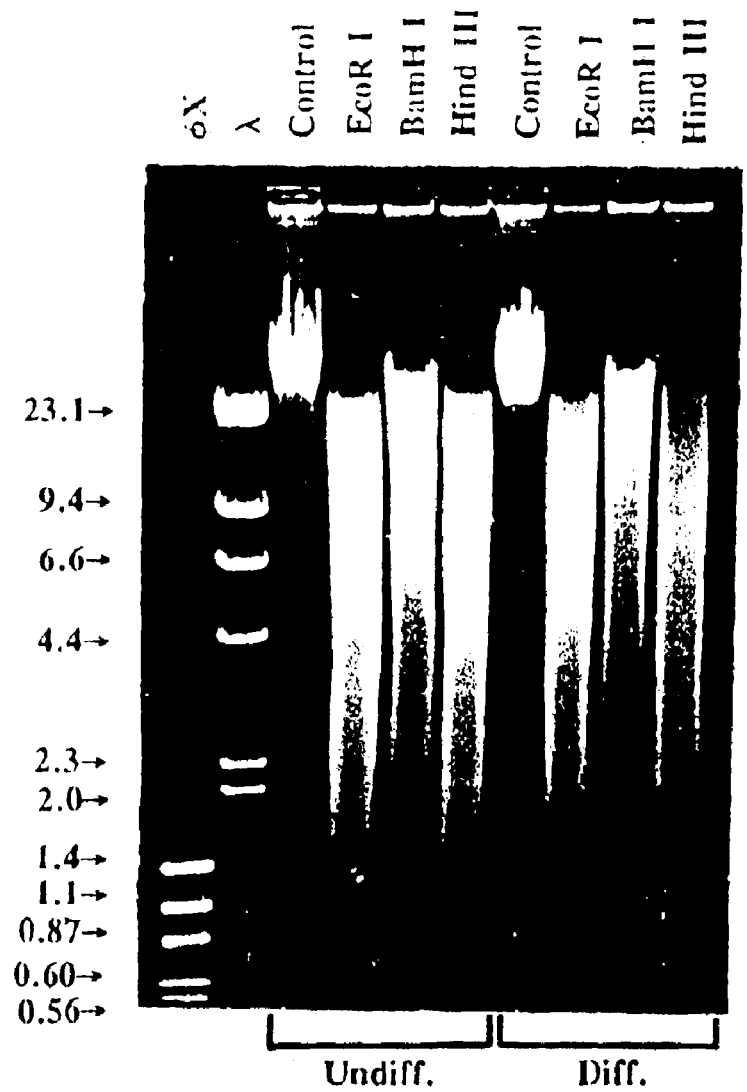
FIG. 3. is an analysis of the DNA profile isolated from undifferentiated (Lanes 3–6) and differentiated (Lanes 7–10) MDS cells.
Figure 4:
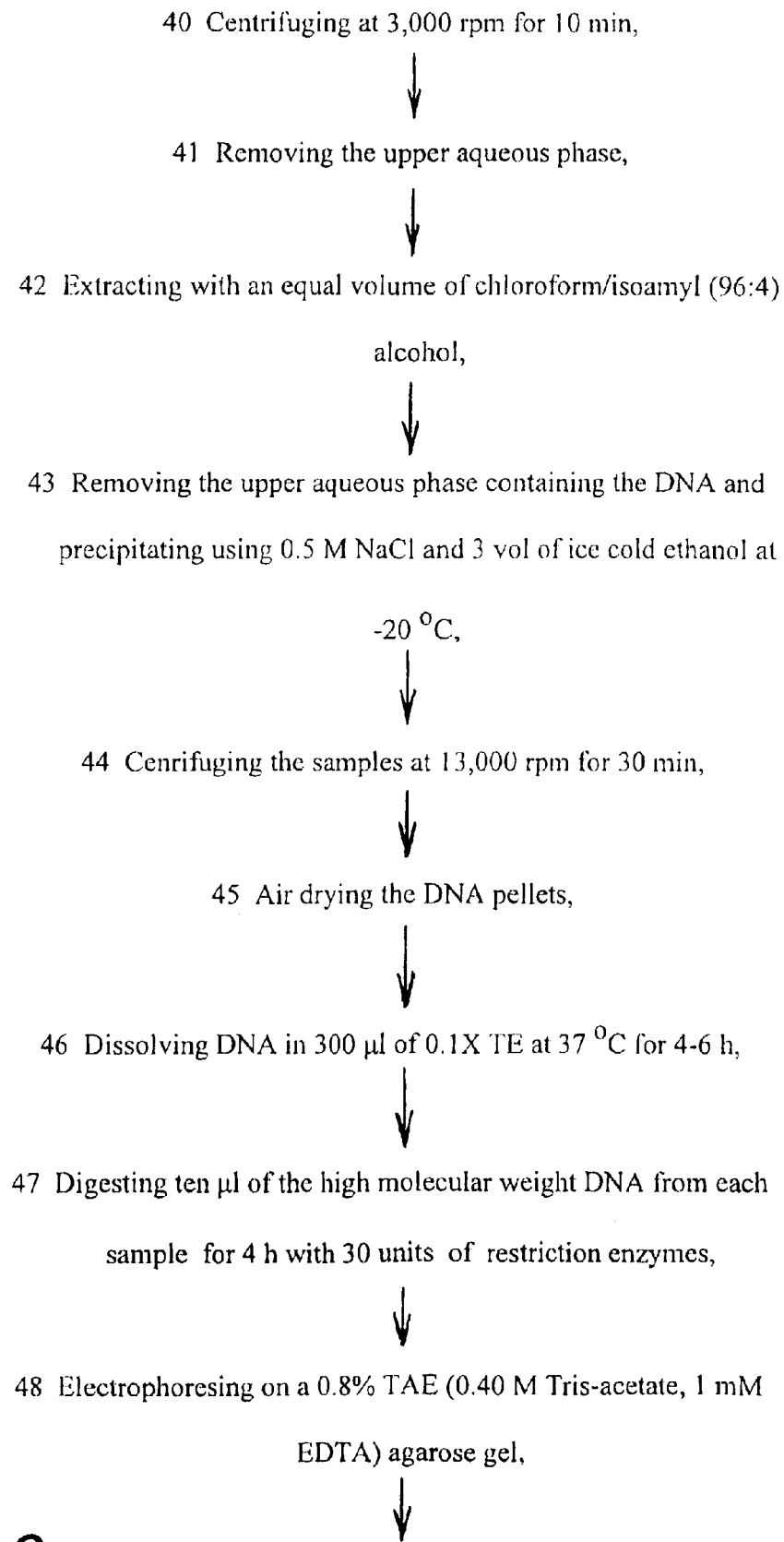
FIGS. 4A–4K show a schematic flow chart outlining the method of the present invention.

Examples of the results obtained through the use of the method of the present invention are shown in FIGS. 1–3. An overall schematic flowchart outlining the method of the present invention is shown in FIG. 4.

FIG. 1. shows activation of NF-αB (Lanes 2,3) and AP-1 (Lanes 9,10) in MDS cells following 4 h treatment with either TNF-α or PMA, as compared with the untreated controls (Lanes 1 and 8) which show the presence of low levels of constitutive NF-κB and AP-1 in this cell line. Nuclear extracts were incubated with either a [γ-$^{32}$P]ATP radiolabeled NF-κB or AP-1 probe for 25 min and the bound complexes were resolved on a 6% native gel for EMSA as described in the Materials and Methods. The specificity of binding to the respective probes was determined using a 50-fold molar excess of either NF-κB (Lanes 4–6) or AP-1 (Lanes 11–13) unlabeled oligonucleotide as competitors which completely removed all the binding, indicating that these bound complexes resulted from the sequence specific DNA-protein interactions. The arrows indicate the induced NF-κB (I) and the AP-1 (III) complexes, respectively, whereas, the constitutive bands (II) and as well as unbound free probe (FP) resulting from the NF-κB (Lane 7) or AP-1 (Lane 14) are also shown.

FIG. 2. is a super shift assay showing the expression of the NF-κB (Lanes 1–10) or AP-1 (Lanes 11–20) protein subunits in MDS cells treated for 4 h with either TNF-α or PMA detected using specific antibodies as compared to the extracts without any antibody (Lanes 1–3 and 11–13). Nuclear extracts were treated for 1.5 h with antibodies before probing with [γ-$^{32}$P]ATP labeled NF-κB or AP-1, and the complexes were resolved by EMSA on a 5% native gel as described in the Materials and Methods. The extracts were incubated with the antibody against NF-κB p65 subunit (Lanes 4–6) showing the shifted complex (I, Lanes 5,6). A reduced bound (III) and a slighlty shifted complex (II, Lanes 8,9) were observed with p50 antibody treatment. The presence of c-Fos complex, (Lanes 14–16) and c-Jun (Lanes 17–19) were demonstrated mainly by the reduction of the bound complexes (V) and a major shifted c-Fos band due to the PMA treatment (IV, Lane 16). Unbound free probe (FP) is also shown for NF-κB (Lane 10) and AP-1 (Lane 20) at the bottom of the gel.

FIG. 3. is an analysis of the DNA profile isolated from undifferentiated (Lanes 3–6) and differentiated (Lanes 7–10) MDS cells. DNA (10 μg per lane) was digested with EcoR I, BamH I or Hind III, (Lanes 4–6, and Lanes 8–10) and compared with the corresponding undigested controls (Lanes 3 and 7) following analysis on a 0.8% TAE agarose gel. Two μg of Hae III digest ΦX174 and Hind III digest λ DNAs were used as molecular size markers (Lanes 1,2), respectively, ranging from 23.1 to 0.56 kb.

FIG. 4. shows an overall schematic flowchart of the method according to the present invention.

4. Discussion

This report describes an improved method for preparing samples of both nuclear and cytoplasmic extracts (data not shown) which is rapid and can be efficiently used in EMSAs with specific DNA sequences. This method offers significant advantages over other published protocols: (1) it is a fast and efficient way to prepare various cellular proteins; (2) it permits multiple sample collection over a short time span for sequential analysis of gene activation; (3) there is no requirement for expensive or specialized equipment such as ultracentrifuges or sonicators; (4) physical contact and manipulation steps are minimized, providing additional safety in the preparation of samples from biologicaly hazardous infectious patients or cells treated with toxic chemical components; and (5), most importantly, this method is capable of isolating proteins and DNAs simultaneously from each sample so that it is possible to analyze the alterations in DNA modification as well as related changes in the transcriptional proteins.

The only major requirements for this procedure are a few buffers, some common reagents and supplies, and an Eppendorf type centrifuge at 4° C. This procedure can be carried out in most research or clinical laboratories. In addition, the protein concentrations of these extracts are usually high enough so that they can be diluted several fold before use in an EMSA. Furthermore, one of the major advantages over previously published protocols (Dignam et al., 1983a,b; Kadonaga and Tjian, 1986; Fiering et al., 1990; Pizzella and Banerjee, 1994) is that these extracts do not require either extensive manipulation after initial collection, or dialysis of the DNAs and proteins to remove salt or other contaminating reagents. The samples prepared at multiple time points offers the advantage that they are processed in the same experimental set up in a short time span which is extremely critical in isolating activated transcription factors from various disease states and pathological conditions. The results showed that highly purified intact proteins and DNAs are obtained by this method (FIGS. 1–3) and are comparable to the results obtained using more elaborate protocols (Dignam, et al., 1983a,b; Sen and Baltimore, 1986a,b; Sambrook, et al., 1989). This procedure also permits the isolation with full biological activity of critical cellular factors involved in gene regulation but which have short half-lives. Another major advantage we have observed is that most of the samples prepared by this method can be frozen quickly at −86° C. and then used more than a year later. Furthermore, the samples are capable of withstanding several freeze-thaw cycles without any noticeable changes or degradation in the level of binding to different radiolabeled probes for a prolonged time. Although we have demonstrated this improved technique using the MDS cell line, we have also prepared samples from various other lymphoid cells, including cells from HIV-1 infected patients and also non-lymphoid cells with equally effective and reproducible results. For example, in the case of human hepatoblastoma HepG2 cells in addition to NF-κB expression following TNF-α treatment (Banerjee, et al., 1989), there was also a strong induction of AP-1 binding with both TNF-α and PMA treatments, and the complexes revealed the expression of both c-Fos and c-Jun subunits (data not shown), which is slightly different from the results obtained from the MDS cells. Furthermore, there was no significant difference in the DNA profile among the undifferentiated and differentiated MDS cells, but we have observed certain changes in the EMSA data among these two groups, which will be published elsewhere. Therefore, this simplified and efficient method will prove applicable and extremely helpful in numerous clinical as well as experimental situations for the analysis of DNA profiles and transcriptional activation. Moreover, the major advantage of this method is to provide the ease of collecting samples, during miltiple stages of evaluation, and analyzing them with a nominal variation at a later time. Furthermore, this isolation method will allow to extract RNAs (ribonucleic acids) as an intermediary product which is also provides an additional advantage. Therefore, this method has proven significant advantage over other protocols being used where all these three basic biological components, namely DNA, RNA and protein, are purified.

With reference to FIG. 4 the Methods for simultaneous isolation of biologically active transcription factors and DNA includes the following steps which are illustrated schematically in FIG. 4.

1 Collecting and maintaining cells at a concentration in the range of 1–2×10$^5$/ml in culture medium, 2 Treating cells with at least one test compound or obtaining the cells from the treated patients, 3 Collecting the cells by scrapping and by centrifuging at 1,000 rpm for 5 min in a table top centrifuge, 4 Washing the cell pellets twice with 5 ml ice cold PBS, (phosphate buffered saline, pH 7.4) by centrifuging the cells again at 1,000 rpm, 5 Resuspending the cell pellets, transferring to a first Eppendorf tube in 1 ml of ice cold PBS, 6 Centrifuging at 2,000 rpm for 5 min at 4° C. removing the PBS processing the cell pellets following according to the protein and DNA isolation steps comprising, 7 Preparing Buffer A: (cell lysis buffer), [20 mM Hepes, pH 7.9, 10 mM NaCl, 3 mM MgCl$_2$, 0.1% NP-40, 10% glycerol, 0.2 mM EDTA, 1 mM dithiothreitol (DTT), 0.4 mM phenylmethylsulfonyl fluoride (PMSF), antipain (1 μg/ml), leupeptin (1 μg/ml)], 8 Preparing Buffer B: (extraction buffer without salt), [20 mM Hepes, pH 7.9, 0.2 mM EDTA, 20% glycerol, 1 mM DTT, 0.4 mM PMSF, antipain (1 μg/ml), leupeptin (1 μg/ml)], 9 Preparing Buffer C: (extraction buffer with salt), [20 mM Hepes, pH 7.9, 400 MM NaCl, 0.2 mM EDTA, 20% glycerol, 1 mM DTT, 0.4 mM PMSF, antipain (1 µg/ml), leupeptin (1 µg/ml)],

10 Preparing Buffer D: (cytoplasmic extraction clarification buffer), [20 mM Hepes, pH 7.9, 400 mM NaCl, 0.2 mM EDTA, 40% glycerol, 1 mM DTT, 0.4 mM PMSF, antipain (1 µg/ml), leupeptin (1 µg/ml)], 11 Performing Simultaneous isolation of protein and DNA comprising the steps of, 12 Resuspending the cell pellets in 100–125 µl (2 pellet vol) of Buffer A, 13 Maintaining the resuspended cell pellets on ice for 10–15 min with occasional tapping, 14 Pelleting the nuclei by centrifuging at 2,000 rpm for 5 min at 4° C., 15 Removing the cytoplasmic supernatant fraction to a second Eppendorf tube, 16 Quick freezing on dry ice in a −86° C. freezer and store for future use, 17 Washing the bottom nuclear fraction with 200–300 µl Buffer B to remove NP-40, 18 Centrifuging at 2,000 rpm for 5 min at 4° C., 19 Resuspending the pelleted nuclei into 100–130 µl high salt Buffer C on ice for 45 min and mixing periodically by tapping to extract the nuclear proteins, 20 Centrifuging the nuclear fraction in an Eppendorf centrifuge at 13,000 rpm for 15 min at 4° C., 21 Removing the supernatents, aliquoted, in 25 µl and quick freezing on dry ice, 22 Storing at −86° C., 23 Quick freezing the remaining pellet containing nucleic acids and other debris, 24 Storing at −86° C., 25 Clarifying the cytoplasmic fraction by adding ⅓ vol of Buffer D to this fraction for 30 min at 4° C. to equilibrate the cytoplasmic proteins with NaCl, 26 Centrifuging at 13,000 rpm for 15 min., 27 Removing and quick freezing the supernatants and storeing at −86° C., 28 Performing DNA extraction and analysis comprising the steps of, 29 Thawing frozen cell pellets from on ice for 10 min, 30 Adding 100 l of Buffer [0.1% SDS, 10 mM Tris-HCl, pH 7.9, 10 mM EDTA, 10 mM NaCl] for 15 min, 31 Mixing using wide bore Eppendorf pipet tips, 32 Adding RNAase A for 2 h at 37° C. with gentle tapping every 30 min, 33 Adding proteinase K [200 l/ml] for 2 h at 37° C. with gentle tapping every 30 min, 34 Extracting with an equal volume of TE (10 mM Tris-HCl, 1 mM EDTA, pH 8.0) saturated phenol, 35 Removing the upper aqueous layer was removed to another tube, 36 Performing back extractions twice with 50 µl of TE, 37 Collecting the DNA solutions in a fresh tube, 38 Adding an equal volume of phenol/chloroform (50:50) mixture, 39 Mixing by inverting repeatedly, 40 Centrifuging at 3,000 rpm for 10 min, 41 Removing the upper aqueous phase, 42 Extracting with an equal volume of chloroform/isoamyl (96:4) alcohol, 43 Removing the upper aqueous phase containing the DNA and precipitating using 0.5 M NaCl and 3 vol of ice cold ethanol at −20° C., 44 Cenrifuging the samples at 13,000 rpm for 30 min, 45 Air drying the DNA pellets, 46 Dissolving DNA in 300 l of 0.1×TE at 37° C. for 4–6 h, 47 Digesting ten 1 of the high molecular weight DNA from each sample for 4 h with 30 units of restriction enzymes, 48 Electrophoresing on a 0.8% TAE (0.40 M Tris-acetate, 1 mM EDTA) agarose gel, 49 Staining the DNA gel with ethidium bromide, 50 Photographing with UV light, 51 Radiolabeling of the sequence specific oligonucleotides comprising the steps of, 52 Synthesizing single stranded oligonucleotides on a DNA synthesizer and annealing with the complimentary strand by combining 4 µg of both strands in a tube with total volume of 30 µl of annealing buffer (5 mM NaCl, 10 mM Tris-HCl and 0.2 mM EDTA), 53 boiling the tubes for 5 min and slowly cooling to room temperature for 6 h, 54 Heating the tubes to 55° C. for 5 min and then cooling on ice for 10 min, 55 Quantitating 4 µl aliquot of the annealed oligos at 260 λ and storing the remainder at −20° C. until radiolabeled, 56 Preparing probes by radiolabeling 200 ng of annealed oligonucleotide in 15 µl of total volume containing 50 µCi of [γ-$^{32}$P]ATP (6,000 Ci/mmol), 20 Units of T4 polynucleotide kinase, and 1.5 µl 10× T4 polynucleotide kinase buffer for 1 h at 37° C., 57 Filling in the 5' over-hang ends with 5 Units of Klenow with 3.0 µl of 10× Klenow buffer and 0.15 mM each of dATP, dCTP, dGTP, and dTTP for 40 min at 37° C. in a reaction volume of 30 µl.

58 Increasing the volume to 1 ml with sterile TE with 200 mM NaCl, pH 8.0, and the labeled oligonucleotides were purified on a NACS Prepac column, to separate the unincorporated nucleotides, 59 Precipating the labeled, purified oligonucleotides overnight with 3 vol absolute ethanol at −20° C.

60 Centrifuging at 13,000 rpm for 1 h and then vacuum drying,

61 Resuspending the labeled oligonucleotide probes in 100 µl of sterile 0.1×TE buffer and storing at −20° C., 62 Electrophoretic mobility shift assay, 63 Incubating 5 µg of nuclear or cytoplasmic extract, for each reaction, with 0.2–0.3 ng of [γ-$^{32}$P]ATP labeled oligonucleotide probe containing either NF-κB sequence (5'-gatccGGGACTTTCCGCTGGGGACTTTCCG-3') (SEQ ID NO 1) or an AP-1 consensus sequence including the PMA responsive element indicated in bold (5'-gatccGTGACTCAGCGCG-3') (SEQ ID NO 2), 64 Adding 3 µg of poly(dI-dC):poly(dI-dC) as a non-specific competitor and incubating with the nuclear extracts for 10 min prior to the addition of the radiolabeled probe, 65 Adding antibodies against p65, p50, c-Fos or c-Jun to the respective binding reactions for supershift assays and incubating at room temperature for 1.5 h, prior to probing with [γ-$^{32}$P]ATP labeled oligonucleotide for an additional 25 min at room temperature, 66 Separating the bound complexes on either a 5% ,for supershift assays, or 6% for analytical purposes, acrylamide/bis (30:1 ratio) native gel as required and runing at 200v for 3.5 h with 0.25×TBE (0.02 M Tris-borate, 0.5 mM EDTA) as running buffer at room temperature, 67 Vacuum drying the gel with heat at 80° C. and exposing them to Kodak X-OMAT film for 3–12 hours, 68 Analyzing the bound and free DNA protein complexes.

The foregong specific embodiments of the present invention as set forth in the specification herein are for illustrative purposes only. Various deviations and modifications may be made within the spirit and scope of the this invention without departing from the main theme thereof.

What is claimed is:

1. A method for simultaneous isolation of biologically active transcription factors and DNA, wherein no ultracentrifugation or sonication is used, comprising the following steps:
   a) collect cells from a culture or from a patient,
   b) washing said cells at least once with PBS,
   c) suspend and maintain said cells in buffer A (cell lysis buffer) for approximately 15 minutes wherein buffer A comprises: 20 mM Hepes, pH 7.9, 10 mM NaCl, 3 mM $MgCl_2$, 0.1% NP-40, 10% glycerol, 0.2 mM EDTA, 1 mM DTT, 0.4 mM PMSF, 1 µg/ml antipain, 1 µg/ml leupeptin,
   d) centrifuge the suspension of step c at approximately 2,000 rpm for approximately 5 min at approximately 4° C.,
   e) remove the upper cytoplasmic supernatant fraction and then clarify this fraction by adding buffer D (cytoplasmic extraction clarification buffer) at approximately 4° C., wherein buffer D comprises: 20 mM Hepes, pH 7.9, 400 mM NaCl, 0.2 mM EDTA, 40% glycerol, 1 mM DTT, 0.4 mM PMSF, 1 µg/ml antipain, 1 µg/ml leupeptin,
   f) centrifuge the clarified fraction formed in step e approximately 13,000 rpm for approximately 15 min,
   g) remove and freeze the top clear supernatant on dry ice then store the frozen top clear supernatant at approximately −86° C.,
   h) wash the bottom nuclear fraction formed at the end of step d with buffer B (extraction buffer without salt) wherein buffer B comprises: 20 mM Hepes, pH 7.9, 0.2 mM EDTA, 20% glycerol 1 mM DTT, 0.4 mM PMSF, 1 µg/ml antipain, 1 µg/ml leupeptin,
   i) centrifuge the mixture formed in step h at approximately 2,000 rpm for approximately 5 minutes at approximately 4° C., thereby pelleting cellular nuclei,
   j) suspend the pelleted nuclei of step i in buffer C (extraction buffer with salt) on ice, tapping the suspended mixture for approximately 45 minutes whereby nuclear proteins are extracted, wherein buffer C comprises: 20 mM Hepes, pH 7.9, 400 mM NaCl, 0.2 mM EDTA, 20% glycerol, 1 mM DTT, 0.4 mM PMSF, 1 µg/ml antipain, 1 µg/ml leupeptin,
   k) centrifuge the mixture formed in step j at approximately 13,000 rpm for approximately 15 minutes, at approximately 4° C.,
   l) remove the top clear supernatant comprising biologically active transcription factors from the bottom nuclear fraction containing nucleic acids, and quick freeze on dry ice and store at approximately −86° C.,
   m) extract DNA from said bottom nuclear fraction.

2. The method of claim 1 wherein the method further includes: the steps of analyzing the biologically active cytoplasmic factors present in the top clear supernatant of step g.

3. The method of claim 1 wherein the step of performing DNA extraction comprises the steps of:
   1) adding buffer containing Tris-HCl, EDTA, NaCl and SDS to the nuclear fraction of step 12,
   2) adding RNAase A followed by proteinase K for approximately 2 hours at approximately 37° C. with gentle tapping,
   3) mixing with an equal volume of Tris-HCl and EDTA buffer saturated phenol,
   4) centrifuging at approximately 3,000 rpm for approximately 10 min, and collecting the upper aquous phase containing DNA,
   5) mixing with equal volume of phenol and chloroform,
   6) centrifuging at approximately 3,000 rpm for approximately 10 min, and collecting the upper aquous phase containing DNA,
   7) mixing with an equal volume of chloroform/isoamyl alcohol prepared at a ratio of 96:4,
   8) centrifuging at approximately 3,000 rpm for approximately 10 min,
   9) collecting the upper aquous phase containing DNA and precipitating using a salt and ethanol,
   10) cenrifuging at approximately 13,000 rpm for approximately 30 min,
   11) removing the upper liquid phase and air drying the bottom DNA pellet,
   12) dissolving the air dried DNA pellets in Tris-HCl and EDTA buffer.

4. The method of claim 1 wherein the method further includes the steps of analyzing the biologically active transcription factors present in the top clear supernatant of step 1.

* * * * *